(12) United States Patent
Aravamudan

(10) Patent No.: US 12,333,393 B2
(45) Date of Patent: Jun. 17, 2025

(54) SYSTEMS AND METHODS FOR ADAPTIVELY IMPROVING THE PERFORMANCE OF LOCKED MACHINE LEARNING PROGRAMS

(71) Applicant: nference, inc., Cambridge, MA (US)

(72) Inventor: Murali Aravamudan, Andover, MA (US)

(73) Assignee: nference, Inc., Cambridge, MA (US)

( * ) Notice: Subject to any disclaimer, the term of this patent is extended or adjusted under 35 U.S.C. 154(b) by 340 days.

(21) Appl. No.: 17/985,777

(22) Filed: Nov. 11, 2022

(65) Prior Publication Data

US 2023/0071353 A1 Mar. 9, 2023

Related U.S. Application Data

(63) Continuation-in-part of application No. 16/908,520, filed on Jun. 22, 2020, now Pat. No. 11,545,242.

(60) Provisional application No. 63/012,738, filed on Apr. 20, 2020, provisional application No. 62/984,989, filed on Mar. 4, 2020, provisional application No. 62/985,003, filed on Mar. 4, 2020, provisional
(Continued)

(51) Int. Cl.
| | |
|---|---|
| G06F 21/62 | (2013.01) |
| G06N 20/00 | (2019.01) |
| G16H 10/60 | (2018.01) |

(52) U.S. Cl.
CPC ......... *G06N 20/00* (2019.01); *G06F 21/6245* (2013.01); *G16H 10/60* (2018.01)

(58) Field of Classification Search
CPC .... G06N 20/00; G06F 21/6245; G16H 10/60; G16H 50/70; G16H 50/20
See application file for complete search history.

(56) References Cited

U.S. PATENT DOCUMENTS

| | | |
|---|---|---|
| 7,542,969 B1 | 6/2009 | Rappaport et al. |
| 9,514,405 B2 | 12/2016 | Chen et al. |

(Continued)

FOREIGN PATENT DOCUMENTS

| | | |
|---|---|---|
| CN | 105938495 A | 9/2016 |
| JP | 2019-536178 A | 12/2019 |

(Continued)

OTHER PUBLICATIONS

AMD Secure Encrypted Virtualization (SEV), https://developer.amd.com/sev/, accessed Sep. 23, 2020 (5 pages).
(Continued)

*Primary Examiner* — Izunna Okeke
(74) *Attorney, Agent, or Firm* — Caldwell Intellectual Property Law

(57) ABSTRACT

Techniques for adaptively improving the performance of a locked machine learning program have been disclosed. In one particular embodiment, the techniques may be realized as a method for enabling a first party to provide a trained machine learning model to a second party, the method comprising receiving the trained machine learning model from the first party, the trained machine learning model being associated with one or more policies defining permissible operations; and constraining the second party to operate the trained machine learning model in a manner that is consistent with said one or more policies.

20 Claims, 7 Drawing Sheets

Related U.S. Application Data application No. 62/962,146, filed on Jan. 16, 2020, provisional application No. 62/865,030, filed on Jun. 21, 2019.

(56) References Cited

U.S. PATENT DOCUMENTS

| | | | |
|---|---|---|---|
| 9,953,095 | B1 | 4/2018 | Scott et al. |
| 10,360,507 | B2 | 7/2019 | Aravamudan et al. |
| 11,062,218 | B2 | 7/2021 | Aravamudan et al. |
| 11,487,902 | B2 | 11/2022 | Ardhanari et al. |
| 11,545,242 | B2 | 1/2023 | Aravamudan |
| 2004/0013302 | A1 | 1/2004 | Ma et al. |
| 2007/0039046 | A1 | 2/2007 | Van Dijk et al. |
| 2008/0118150 | A1 | 5/2008 | Balakrishnan et al. |
| 2008/0243825 | A1 | 10/2008 | Staddon et al. |
| 2009/0116736 | A1 | 5/2009 | Neogi et al. |
| 2011/0255788 | A1 | 10/2011 | Duggan et al. |
| 2011/0307460 | A1 | 12/2011 | Vadlamani et al. |
| 2013/0132331 | A1 | 5/2013 | Kowalczyk et al. |
| 2015/0161413 | A1 | 6/2015 | Calem et al. |
| 2015/0254555 | A1 | 9/2015 | Williams, Jr. et al. |
| 2016/0105402 | A1 | 4/2016 | Soon-Shiong et al. |
| 2016/0247307 | A1 | 8/2016 | Stoop et al. |
| 2017/0032243 | A1 | 2/2017 | Corrado et al. |
| 2017/0061326 | A1 | 3/2017 | Talathi et al. |
| 2017/0091391 | A1 | 3/2017 | LePendu |
| 2018/0060282 | A1 | 3/2018 | Kaljurand |
| 2018/0212971 | A1 | 7/2018 | Costa |
| 2019/0319982 | A1 | 10/2019 | Durand et al. |
| 2019/0354883 | A1 | 11/2019 | Aravamudan et al. |
| 2020/0082270 | A1* | 3/2020 | Gu .................. G06N 3/045 |
| 2020/0402625 | A1 | 12/2020 | Aravamudan et al. |
| 2021/0019287 | A1 | 1/2021 | Prasad et al. |
| 2021/0224264 | A1 | 7/2021 | Barve et al. |
| 2021/0248268 | A1 | 8/2021 | Ardhanari et al. |
| 2022/0050921 | A1 | 2/2022 | LaFever et al. |
| 2022/0138599 | A1 | 5/2022 | Aravamudan et al. |
| 2024/0320348 | A1* | 9/2024 | Williams .......... G06F 21/602 |

FOREIGN PATENT DOCUMENTS

| | | |
|---|---|---|
| WO | WO-2015084759 A1 | 6/2015 |
| WO | WO-2015149114 | 10/2015 |
| WO | WO-2018057945 | 3/2018 |
| WO | WO-2020257783 | 12/2020 |
| WO | WO-2021011776 | 1/2021 |
| WO | WO-2021146694 A1 | 7/2021 |
| WO | WO-2021178689 | 9/2021 |

OTHER PUBLICATIONS

Arora, S. et al., "A Simple But Tough-To-Beat Baseline for Sentence Embeddings", ICLR, 2017 (16 pages).
AWS Key Management Service (KMS), https://aws.amazon.com/kms, accessed Jan. 20, 2021 (3 pages).
AWS Key Management Service (KMS), https://aws.amazon.com/kms, accessed Sep. 23, 2020 (6 pages).
Bartunov, S. et al., "Breaking Sticks And Ambiguities With Adaptive Skip-Gram", retrieved online from URL :< https://arxiv.org/pdf/1502.07257.pdf>, [cs.CL], Nov. 15, 2015 (15 pages).
Bojanowski, P. et al., "Enriching Word Vectors with Subword Information", retrieved online from URL :< https://arxiv.org/pdf/1607.04606.pdf>, [cs.CL], Jun. 19, 2017 (12 pages).
Confidential Computing Consortium, "What is the Confidential Computing Consortium?", https://confidentialcomputing.io, accessed Sep. 24, 2020 (2 pages).
De Guzman, C.G. et al., "Hematopoietic Stem Cell Expansion and Distinct Myeloid Developmental Abnormalities in a Murine Model of the *AML1-ETO* Translocation", Molecular and Cellular Biology, 22(15):5506-5517, Aug. 2002 (12 pages).
Desaulier, G., " A lesson from associative learning: asymmetry and productivity in multiple-slot constructions", Corpus Linguistic and Linguistic Theory, 12(2): 173-219, 2016, submitted Aug. 13, 2015, <http://www.degruyter.com/view/j/cllt.2016.12.issue-2/cllt-2015-0012/cllt-2015-0012.XML?format=INT>. <10.1515/cllt-2015-0012>. <halshs-01184230>, (32 pages).
Devlin, J. et al., "BERT: Pre-training of Deep Bidirectional Transformers for Language Understanding", arXiv:1810.04805v2 [cs.CL], May 24, 2019 (16 pages).
Divatia, A., "The Fact and Fiction of Homomorphic Encryption", Dark Reading, www.darkreading.com/attacks-breaches/the-fact-and-fiction-of-homomorphic-encryption/a/d-id/1333691, Jan. 22, 2019 (3 pages).
Dwork, C., "Differential Privacy: A Survey of Results", Lecture Notes in Computer Science, vol. 4978, pp. 1-19, 2008 (19 pages).
Ferraiuolo, A. et al., "Komodo: Using verification to disentangle secure-enclave hardware from software", SOSP '17, Shanghai, China, pp. 287-305, Oct. 28, 2017 (19 pages).
Garten, Y. et al., "Pharmspresso: a text mining tool for extraction of pharmacogenomic concepts and relationships from full text", BMC Bioinformatics, 10(Suppl. 2):S6, Feb. 5, 2009 (9 pages).
Genkin, D. et al., "Privacy in Decentralized Cryptocurrencies", Communications of the ACM, 61(6):78-88, Jun. 2018 (11 pages).
Hageman, G.S. et al., "A common haplotype in the complement regulatory gene factor H (*HF1 / CFH*) predisposes individuals to age-related macular degeneration", PNAS, 102(20):7227-7232, May 17, 2005 (6 pages).
Ikeda, T. et al., "Anticorresponding mutations of the *KRAS* and *PTEN* genes in human endometrial cancer", Oncology Reports, 7: 567-570, published online May 1, 2000 (4 pages).
Intel, "What is Intel® SGX?", http://www.intel.com/content/www/us/en/architecture-and-technology/software-guard-extensions.html, accessed Sep. 23, 2020 (8 pages).
International Preliminary Report on Patentability issued in International Application No. PCT/US2021/020906, Sep. 15, 2022 (9 pages).
International Search Report and Written Opinion issued by the European Patent Office as International Searching Authority in International Application PCT/US2017/053039, dated Dec. 20, 2017 (15 pages).
International Search Report and Written Opinion issued by the U.S. Patent and Trademark Office as International Searching Authority issued in International Application No. PCT/US21/20906, dated May 19, 2021 (10 pages).
International Search Report and Written Opinion issued by U.S. Patent and Trademark Office as International Searching Authority in International Application No. PCT/US20/42336, dated Sep. 30, 2020 (10 pages).
International Search Report and Written Opinion issued by U.S. Patent and Trademark Office as International Searching Authority, for International Application No. PCT/US20/38987, dated Nov. 9, 2020 (26 pages).
Joulin, A. et al., "Bag of Tricks for Efficient Text Classification", retrieved online from URL:<https://arXiv.org/pdf/1607.01759v3.pdf>, [cs.CL], Aug. 9, 2016 (5 pages).
Kiros, R. et al., "Skip-Thought Vectors", retrieved online from URL:<https://arXiv.org/abs/1506.06726v.1>, [cs.CL], Jun. 22, 2015 (11 pages).
Kolte, P. "Why Is Homomorphic Encryption Not Ready For Primetime?", Baffle, https://baffle.io/blog/why-is-homomorphic-encryption-not-ready-for-primetime/, Mar. 17, 2017 (4 pages).
Korger, C., "Clustering of Distributed Word Representations and its Applicability for Enterprise Search", Doctoral Thesis, Dresden University of Technology, Faculty of Computer Science, Institute of Software and Multimedia Technology, Matriculation Nr. 3703541, submitted Jul. 28, 2016 (116 pages).
Kutuzov, A. et al., "Cross-lingual Trends Detection for Named Entities in News Texts with Dynamic Neural Embedding Models", Proceedings of the NewsIR'16 Workshop at ECIR, Padua, Italy, Mar. 20, 2016 (6 pages).
Le, Q. et al., "Distributed Representations of Sentences and Documents", Proceedings of the 31st International Conference of Machine Learning, Beijing, China, vol. 32, 2014 (9 pages).

(56) References Cited

OTHER PUBLICATIONS

Li, H. et al., "Cheaper and Better: Selecting Good Workers for Crowdsourcing," retrieved online from URL: https://arXiv.org/abs/1502.00725v.1, pp. 1-16, Feb. 3, 2015 (16 pages).
Ling, W et al., "Two/Too Simple Adaptations of Word2Vec for Syntax Problems", retrieved online from URL:<https://cs.cmu.edu/~lingwang/papers/naacl2015.pdf>, 2015 (6 pages).
Maxwell, K.N. et al., "Adenoviral-mediated expression of Pcsk9 in mice results in a low-density lipoprotein receptor knockout phenotype", PNAS, 101(18):7100-7105, May 4, 2004 (6 pages).
Mikolov, T. et al., "Distributed Representations for Words and Phrases and their Compositionality", retrieved online from URL:https://arXiv.org/abs/1310.4546.v1 [cs.CL], Oct. 16, 2013 (9 pages).
Mikolov, T. et al., "Efficient Estimation of Word Representations in Vector Space", retrieved online from URL: https://arXiv.org/abs/1301.3781v3 [cs.CL] Sep. 7, 2013 (12 pages).
Murray, K., "A Semantic Scan Statistic for Novel Disease Outbreak Detection", Master's Thesis, Carnegie Mellon University, Aug. 16, 2013 (68 pages).
Neelakantan, A., et al., "Efficient Non-parametric Estimation of Multiple Embeddings per Word in Vector Space," Department of Computer Science, University of Massachusetts, (2015) (11 pages).
Pennington, J. et al., "GloVe: Global Vectors for Word Representation", retrieved online from URL:<https://nlp.stanford.edu/projects/glove.pdf>, 2014 (12 pages).
Rajagopalan, H., et al., "Tumorigenesis: RAF/RAS oncogenes and mismatch-repair status", Nature, 418:934, Aug. 29, 2002 (1 page).
Rajasekharan, "Unsupervised NER using BERT", [accessed Jun. 10, 2021], Toward Data Science, <URL: https://towardsdatascience.com/unsupervised-ner-using-bert-2d7af5f90b8a>, Feb. 28, 2020 (27 pages).
Shamir, A. "How to Share a Secret", Communications of the ACM, 22(11):612-613, Nov. 1979 (2 pages).
Shweta, Fnu et al., "Augmented Curation of Unstructured Clinical Notes from a Massive EHR System Reveals Specific Phenotypic Signature of Impending COVID-19 Diagnosis", https://www.medrxiv.org/content/10.1101/2020.04.19.20067660v3.full, accessed Sep. 24, 2020 (24 pages).
Van Mulligen, E.M. et al., "The EU-ADR corpus: Annotated drugs, diseases, targets, and their relationships", Journal of Biomedical Informatics, 45:879-884, published online Apr. 25, 2012 (6 pages).
Wieting, J. et al., "Revisiting Recurrent Networks for Paraphrastic Sentence Embeddings", retrieved online from URL:<https://arXiv.org/pdf/1705.00364v1.pdf>, [cs.CL], Apr. 30, 2017 (12 pages).
Yao, Z. et al., "Dynamic Word Embeddings for Evolving Semantic Discovery", WSDM 2018, Marina Del Rey, CA, USA, Feb. 5-9, 2018 (9 pages).
Zuccon, G., et al., "Integrating and Evaluating Neural Word Embeddings in Information Retrieval", ADCS, Parramatta, NSW, Australia, Dec. 8-9, 2015 (8 pages).
Daniel Genkin et al: "Privacy in decentralized cryptocurrencies", Communications of the ACM, Association for Computing Machinery, Inc, United States, vol. 61, No. 6, May 23, 2018 (May 23, 2018), pp. 78-88, XP058407634, ISSN: 0001-0782, DOI: 10.1145/3132696.
Bradley Malin: "Guidance Regarding Methods for De-identification of Protected Health Information in Accordance with the Health Insurance Portability and Accountability Act (HIPAA) Privacy Rule", Nov. 26, 2012 (Nov. 26, 2012), XP055463396, Retrieved from the Internet: URL:https://www.hhs.gov/sites/default/files/ocr/privacy/hipaa/understanding/coveredentities/De-identification/hhs_deid_guidance.pdf [retrieved on Mar. 28, 2018].
Devlin Jacob et al: "BERT: Pre-training of Deep Bidirectional Transformers for Language Understanding", Oct. 11, 2018 (Oct. 11, 2018), XP055968792, Retrieved from the Internet: URL:https://www.arxiv.org/pdf/1810.04805v1.pdf [retrieved on Oct. 6, 2022].
Rajasekharan Ajit: "Unsupervised NER using BERT", Towards Data Science, Feb. 28, 2020 (Feb. 28, 2020), XP093054321, Retrieved from the Internet: URL:https://towardsdatascience.com/unsupervised-ner-using-bert-2d7af5f90b8a [retrieved on Jun. 14, 2023].
European Search Report; EP 24 17 9988; By: Maenpaa, Jari; Sep. 2, 2024.

\* cited by examiner

SYSTEMS AND METHODS FOR ADAPTIVELY IMPROVING THE PERFORMANCE OF LOCKED MACHINE LEARNING PROGRAMS

RELATED APPLICATIONS

This application is a continuation-in-part of U.S. Non-Provisional application Ser. No. 16/908,520, entitled "Systems and Methods for Computing with Private Healthcare Data," filed Jun. 22, 2020 which claims priority to U.S. Provisional Application No. 62/865,030, entitled "Systems and Methods for Selective Information Masking in Text," filed Jun. 21, 2019, U.S. Provisional Application No. 62/962,146, entitled "Systems and Methods for Retrieving Information Responsive to a Query," filed Jan. 16, 2020, U.S. Provisional Application No. 62/984,989, entitled "Systems and Methods for Selective Information Masking in Text," filed Mar. 4, 2020, U.S. Provisional Application No. 62/985,003, entitled "Pipelined Federated Architecture for Computing with Private Healthcare Data," filed Mar. 4, 2020, and U.S. Provisional Application No. 63/012,738, entitled "Systems and Methods for Augmented Curation and Temporal Discrimination of Health Records," filed Apr. 20, 2020, each of which is incorporated by reference herein in its entirety.

FIELD OF THE DISCLOSURE

The present disclosure relates generally to protecting data privacy and intellectual property of computer programs with particular emphasis on cases wherein such data or programs are shared between distinct entities such as enterprises and corporations.

BACKGROUND

Algorithms used in predictive analytics and machine learning have progressed to the point where approvals may be obtained from regulatory bodies such as the FDA (Food and Drug Administration) for the software to be used as a diagnostic medical device (SaMD). When used as such, the resulting ecosystem involves multiple parties comprising of the software/device provider, the patient, the diagnostic center provider, and the platform provider (on which the software/device runs). Each of these parties have concerns that need to be addressed for this nascent use case to succeed.

Furthermore, a property of an ecosystem that succeeds in protecting the interests of the various parties allows the SaMD to adapt its learning capabilities to real world data.

Therefore, a technology that protects and manages the interests of the various parties involved in provisioning Software as a Medical Device (SaMD) would be of enormous benefit to commercial activities and members of society.

Figure 1:
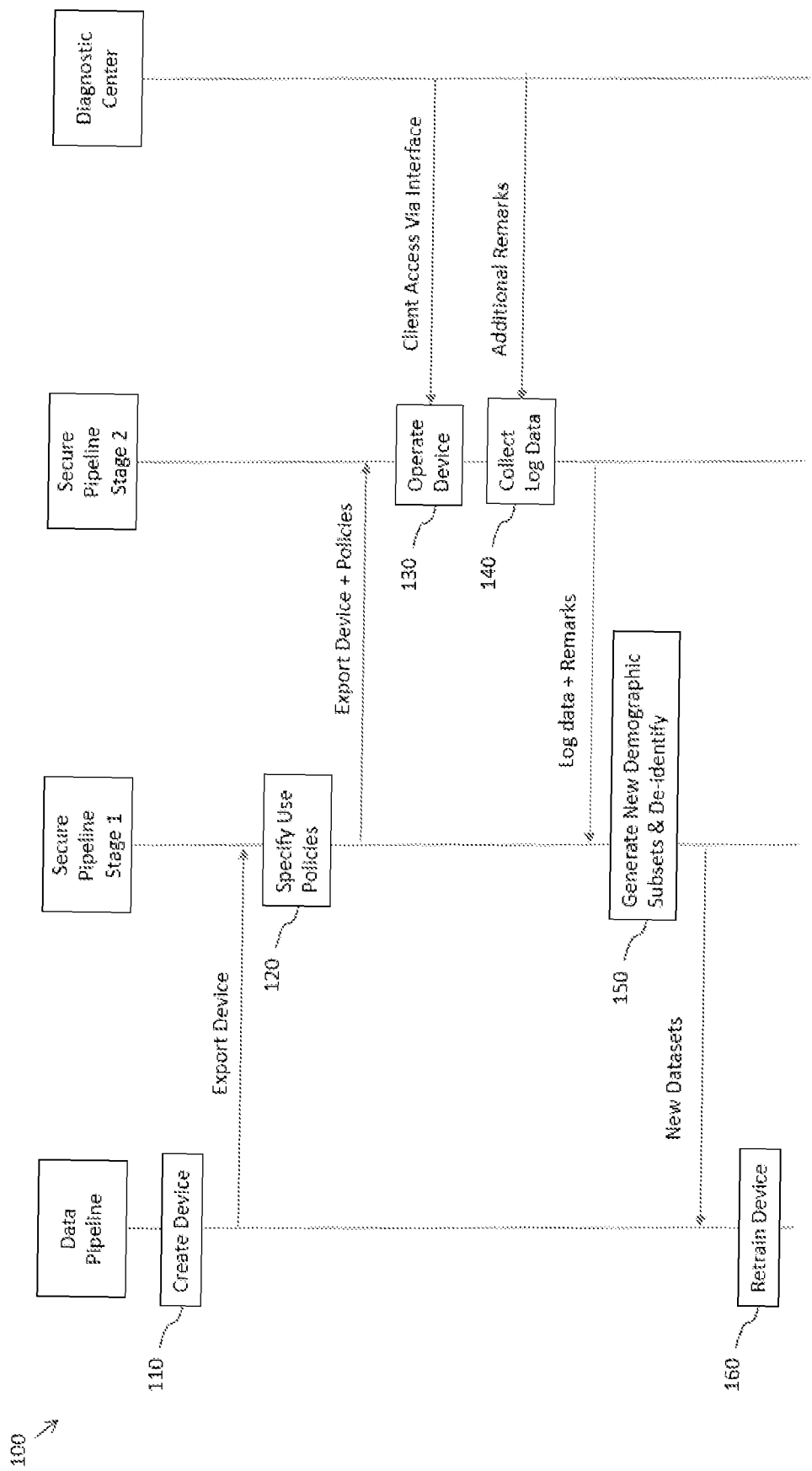
FIG. 1 is a simplified diagram of a method for adaptively improving the performance of a locked machine learning program according to some embodiments.

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

A computer program is said to learn from experience E with respect to some task T and some performance measure P, if its performance on T, as measured by P, improves with experience E.

Consider by way of example a computer program whose task is to flag spam emails. Given an input email (or a collection of emails) the task, T, for the program is to label the input email as "spam" or "not spam." A possible performance measure for this program may be to tabulate the percentage of correctly labeled emails.

Assume the computer program is installed and its performance is measured as, say X %, on actual input emails. A known collection E of emails is then input to the program which processes them. Here the word "known" is indicates that the correct labels to assign to the emails in the collection are known. After the processing is complete, the program is reinstalled, it processes actual input emails, and its performance is measured as, say Y %. If Y>X, then the program can be said to have learned from the set E.

The set E may be referred to as the training set or that the set E is used to train the computer program. The performance P of the computer program can also be referred to as locked with respect to (set) E.

Turning to a different example, consider a program that has been trained to detect pulmonary hypertension in patients. That is, given input data related to the patient (e.g., electrocardiogram EKG of the patient), the program labels the patient as having indications of pulmonary hypertension with a performance measure, P, say 65%.

Stating the performance measure without reference to the locked set upon which the program was trained could be misleading. For example, the samples in the training set could be (strongly) biased towards a certain demographic group that is different from the patient's demographic group.

However, the value of the real-world data (belonging to the patient) to the performance of the computer program is that it introduces the notion of adaptive learning in which the performance of the program changes due to the addition of real-world data (samples). The real-world samples can be referred to as the retraining set.

If the patient data adds to the biased demographic group in the locked set E, it may be used to provide support to the existing performance measure of the (machine learning) program. If the patient data relates to a non-biased demographic group in the set E, it may be used to maintain or improve the performance measure while covering more demographic groups.

By slicing and dicing the real-world samples according to demographic groups, the performance measure of a (machine learning) program with respect to a locked set may be maintained or improved while expanding the demographic groups contained in the original locked set.

Furthermore, the slicing and dicing may be performed by methods referred to herein as heuristic set manipulation methods or algorithms applied to re-training datasets.

The present disclosure is described with respect to a healthcare embodiment without limitation.

In embodiments, a (machine learning) program, M, is trained using an input training set, E, by a program providing entity. (For example, the program providing entity may be an enterprise engaged in software development activities.) The program M is provided to a serving entity which deploys M to process input requests. (For example, the serving entity may be a diagnostic center.) Such an arrangement may generally be referred to as Software as Medical Device (SaMD) service.

The program providing entity requires that the program M not be copied, altered, or duplicated by any party while M is deployed. The serving entity requires that the program M be made available with an initial performance measure and to maintain the initial performance measure while in operation.

The program M is configured to output (at specified or unspecified time intervals) a record (referred to as a log) of its operation, including but not limited to various input samples provided during the operational phase. Furthermore, the serving entity is provided a capability to add remarks to the samples contained in the log and that these additions be done only by authenticated user accounts. Note that the log dataset may contain PHI (Personal Health Information) data.

The serving entity is provided a capability that causes the log dataset to be provided to the program provider.

The program provider manipulates the log dataset using heuristic set manipulation methods without violating regulations related to PHI data.

Recently available hardware leverages cryptographic elements to create Secure Enclaves (SE). A SE may be visualized as a collection of inter-connected processes that are protected (the memory content of the processes is encrypted using keys available only from the underlying computing platform) and isolated (no other process has access to these processes). SEs use Public Key Infrastructure (PKI) embodied in firmware of the underlying platform to dictate and enforce access policies. A computation being carried out by inter-connected SEs may thus be considered as a secure computation in the sense that data and logic associated with said computation may be encrypted and all decryptions being only allowed to happen inside the SE. The computation is thus not accessible by any parties/programs external to SE.

U.S. patent application Ser. No. 16/908,520 shows exemplary implementations wherein data pipelines are constructed whose individual stages use SE technology. Such data pipelines may then be referred to as secure data pipelines and said to achieve end-to-end chain of trust.

In embodiments, the technology of secure enclaves is used to implement some of the elements of the present disclosure.

FIG. 1 is a simplified diagram of a method 100 for adaptively improving the performance of a locked machine learning program according to some embodiments. As shown in FIG. 1, at process 110, a program/device provider may train/prepare a computer program as a SaMD whose performance is defined with respect to a determined locked training set. At process 120, the device may be programmed with policies that define permissible operations and actions. The device provider may cause the program (typically referred to as a model in this phase) to be injected into a (first) stage of a secure data pipeline. The first stage prepares the device/model to make it available to the second stage. The second stage of the secure data pipeline is managed by the diagnostic center which receives the device and may now operate it (process 130). Note that the device as received by the diagnostic center is encrypted and runs in a SE and may thus only be used through a specially configured API. The device provider may specify policies that authorize access to the device, its operation and charging. The diagnostic center and any other party or computer program/process is unable to copy, duplicate or inspect the program since it resides inside the SE in an encrypted form.

At process 140, the device may be configured to output retraining data based on its operations (e.g., an operations log). This dataset is encrypted by the SE using keys provided by the device provider. The diagnostic center is further provided the capability to add remarks to the log dataset. An authentication mechanism restricts remarks to be added only by signed user accounts.

The diagnostic center may then provide the encrypted log dataset back to the device provider's SE. (That is, the data pipeline is run in the backward direction, from the second to the first stage.) At process 150, the device provider's SE is configured to decrypt the log dataset (using its keys) and runs a heuristic method to create a collection of demographic samples with respect to the original locked dataset. That is, the log dataset is split into one or more demographic subsets distinct from the original locked dataset. (Note that the algorithm may use heuristics based on the a priori knowledge of the device provider to construct demographic datasets that vary from the original locked dataset.)

Next, a de-identifying algorithm is run. The de-identifying algorithm removes the PHI (Personal Health Information) and decrypts the data in all the demographic subsets. The resulting de-identified and decrypted subsets may then be exported to the device provider's IT infrastructure where, at process 160, it may be used for retraining with respect to the newly generated demographic dataset. Thus, the original retraining dataset is only accessible to the device provider in encrypted form and, hence, protects both the device and diagnostic center providers.

Figure 2:
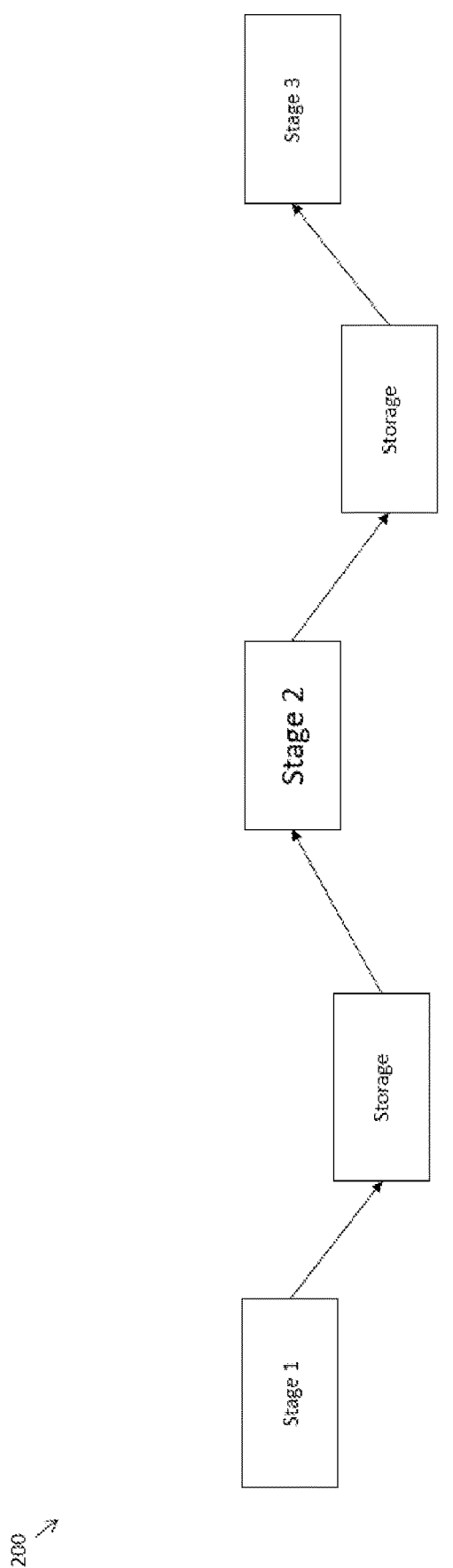
FIGS. 2 and 3 are simplified diagrams of data pipelines according to some embodiments.
Figure 3:
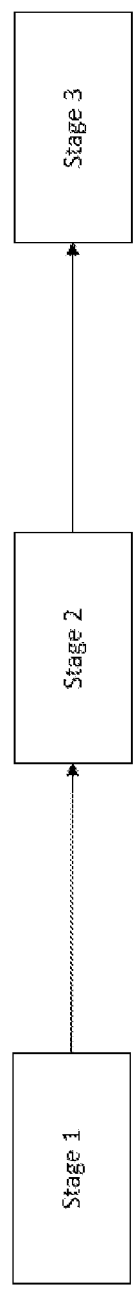

FIGS. 2 and 3 are simplified diagrams of data pipelines 200 and 300, respectively, according to some embodiments. Data pipelines 200 and 300 are generally similar, except data pipeline 200 is shown with storage nodes between pipeline stages, and data pipeline 300 is shown without the storage nodes. In some embodiments consistent with FIG. 1, the stages 1, 2, and 3 of data pipelines 200 and 300 may respectively correspond to the data pipeline, secure pipeline stage 1, and secure pipeline stage 2 used to carry out method 100.

Figure 4:
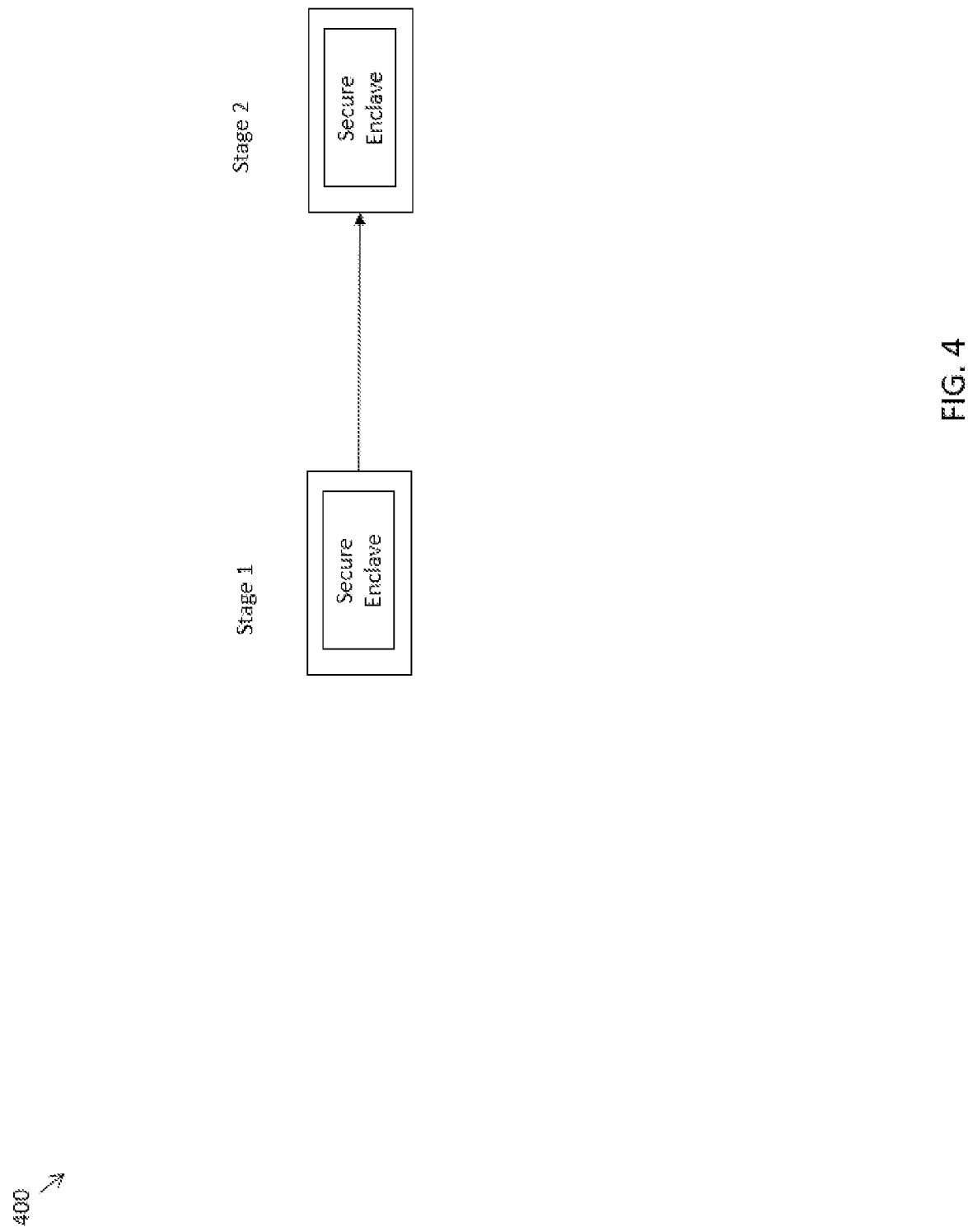
FIG. 4 is a simplified diagram of a secure data pipeline according to some embodiments.

FIG. 4 is a simplified diagram of a secure data pipeline 400 according to some embodiments. In some embodiments consistent with FIG. 1, the stages 1 and 2 of data pipeline 400 may respectively correspond to secure pipeline stage 1 and secure pipeline stage 2 used to carry out method 100. As shown in FIG. 4, each stage of secure data pipeline 400 includes a secure enclave. It is to be understood that FIGS. 1 and 4 are illustrative and that various alternative embodiments are contemplated. For example, secure data pipeline 400 may include more than two stages, in which case stage 1 and 2 may correspond more generally to the (n−1) and nth stages of the n-stage secure data pipeline. For simplicity, storage nodes are not shown between the pipeline stages but may be included in some embodiments.

Figure 5:
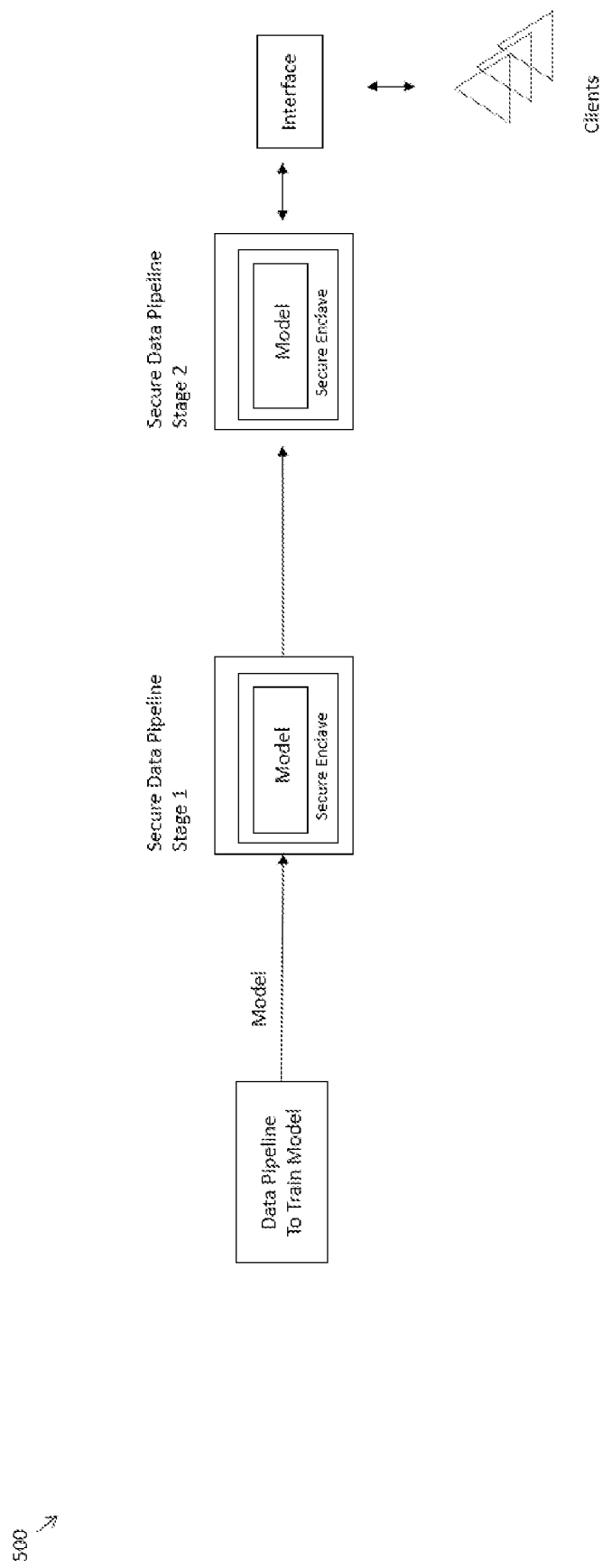
FIG. 5 is a simplified diagram of a secure data pipeline used to deliver Software as a Medical Device (SaMD) according to some embodiments.

FIG. 5 is a simplified diagram of a secure data pipeline 500 used to deliver a SaMD (also referred to as a "model") according to some embodiments. In some embodiments consistent with FIG. 1, the data pipeline, secure data pipeline stage 1, and secure data pipeline stage 2 of secure data pipeline 500 may respectively correspond to similarly named pipeline stages used to carry out method 100. As shown in FIG. 5, each of the secure data pipeline stages 1 and 2 of secure data pipeline 500 includes a secure enclave. The SaMD (model) is transferred from the data pipeline to the secure enclave of secure data pipeline stage 1, and from the secure enclave of secure data pipeline stage 1 to the secure enclave of secure data pipeline stage 2. An interface associated with secure data pipeline stage 2 allows clients (e.g., authenticated users associated with a diagnostic center receiving the SaMD) to access the SaMD (model) in secure data pipeline stage 2 (e.g., as described for process 130 of method 100). For simplicity, storage nodes are not shown between the pipeline stages but may be included in some embodiments.

Figure 6:
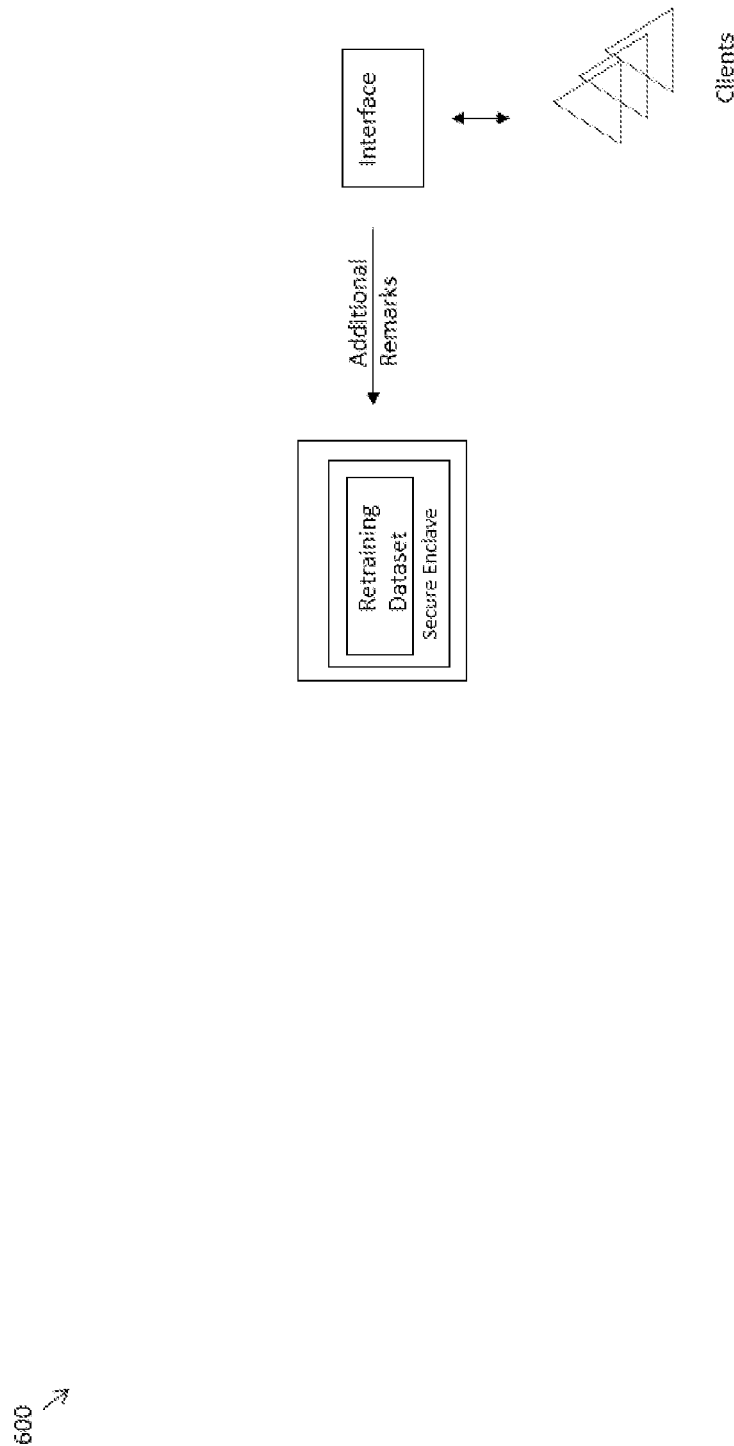
FIG. 6 is a simplified diagram of a secure data pipeline stage configured to allow clients to add remarks to a retraining dataset according to some embodiments.

FIG. 6 is a simplified diagram of a secure data pipeline stage 600 configured to allow clients to add remarks to a retraining dataset according to some embodiments. In some embodiments consistent with FIG. 1, secure data pipeline stage 600 may correspond to secure data pipeline stage 2 used to carry out method 100. As shown in FIG. 6, an interface associated with secure data pipeline stage 600 allows clients (e.g., authenticated users associated with a diagnostic center receiving the SaMD) to add remarks to a retraining data set that is under the control of a secure enclave in secure data pipeline stage 600 (e.g., as described for process 140 of method 100).

Figure 7:
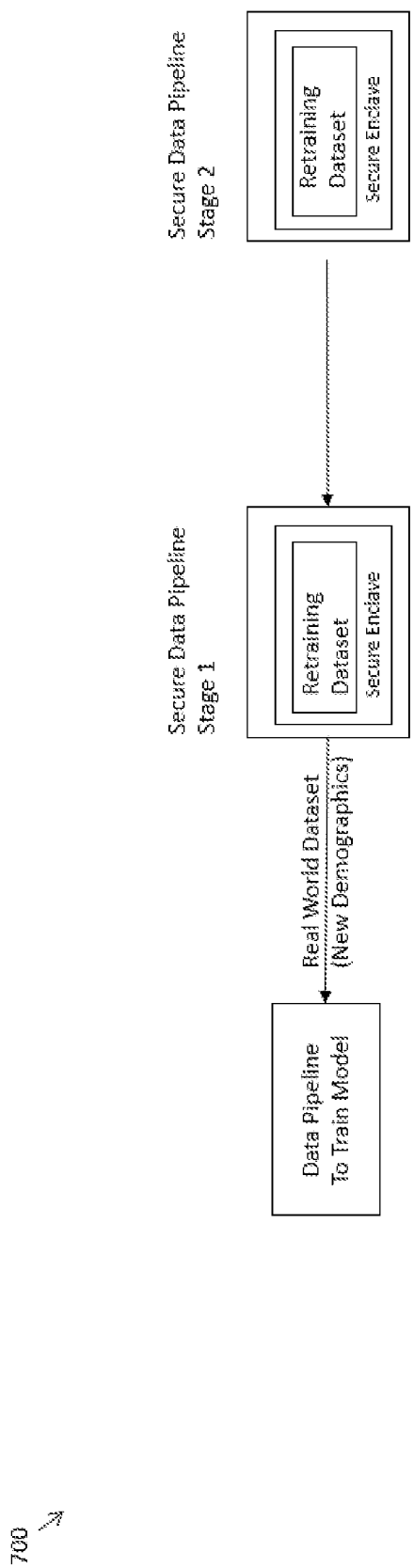
FIG. 7 is a simplified diagram of a secure data pipeline used to deliver a retraining dataset according to some embodiments.

FIG. 7 is a simplified diagram of a secure data pipeline 700 used to deliver a retraining dataset according to some embodiments. In some embodiments consistent with FIG. 1, the data pipeline, secure data pipeline stage 1, and secure data pipeline stage 2 of secure data pipeline 700 may respectively correspond to similarly named pipeline stages used to carry out method 100. As shown in FIG. 7, each of the secure data pipeline stages 1 and 2 of secure data pipeline 700 includes a secure enclave. The retraining dataset is transferred from the secure enclave of secure data pipeline stage 2 to the secure enclave of secure data pipeline stage 1, and from the secure enclave of secure data pipeline stage 1 to the data pipeline. At secure data pipeline stage 1, new demographics may be added to the retraining dataset (e.g., as described for process 150 of method 100). Once delivered, the data pipeline may use the retraining dataset to train the SaMD (model) for improved performance (e.g., as described for process 160). For simplicity, storage nodes are not shown between the pipeline stages but may be included in some embodiments.

In some embodiments, secure enclave technology permits the generation of digital certificates that attest to the integrity of the underlying secure enclaves. One is thus ensured that the secrets are preserved by a secure enclave. Since all data and programs are encrypted while external to a secure enclave, and since the assets are only decrypted inside a secure enclave, the attestation of the integrity of the decryption keys is a testament to the preservation of the contents inside a secure enclave. And since the attestation records generated by a secure enclave are independent of the platform provider, such records attest to the platform provider being a disinterested party.

By collecting the attestation records generated by one or more secure enclaves along with the keys undertaking any actions by any actor (program or user) on the contents of the secure enclaves, one can identify and attest all actions taken by all actors. Such a trail is sometimes called a verifiable audit log.

Verifiable audit logs, when provided to a third party, allow independent verification of the integrity of the contents and actions thereupon in a secure enclave.

In this manner, regulatory bodies may use verifiable audit logs to ascertain that all policies (encapsulated in computer programs) were satisfied by actions and actors with respect to operations on the contents of a given collection of secure enclaves.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Techniques for adaptively improving the performance of a locked machine learning program have been disclosed. In one particular embodiment, the techniques may be realized as a method for enabling a first party to provide a trained machine learning model to a second party, the method comprising receiving the trained machine learning model from the first party, the trained machine learning model being associated with one or more policies defining permissible operations; and constraining the second party to operate the trained machine learning model in a manner that is consistent with said one or more policies.

In accordance with other aspects of this particular embodiment, the method further comprises encapsulating the trained machine learning model within a secure enclave.

In accordance with other aspects of this particular embodiment, the secure enclave is connected to a first stage of a secure data pipeline.

In accordance with other aspects of this particular embodiment, the first stage accepts an output of another data pipeline.

In accordance with other aspects of this particular embodiment, the first stage is connected to an input of a second stage data pipeline.

In accordance with other aspects of this particular embodiment, the method further comprises collecting operational data associated with the second party operating the trained machine learning model; and storing the operational data under control of a secure enclave thereby restricting access to the operational data to one or more authenticated parties.

In accordance with other aspects of this particular embodiment, the method further comprises permitting additional data to be added to the operational data by the one or more authenticated parties.

In accordance with other aspects of this particular embodiment, the method further comprises attaching at least one digital certificate to the additional data.

In accordance with other aspects of this particular embodiment, the method further comprises collecting, by a program operating in a secure enclave serving as a nth-stage of a secure pipeline, a dataset; and transmitting said dataset to the (n−1) stage of said secure pipeline.

In accordance with other aspects of this particular embodiment, the (n−1) stage of said secure pipeline processes the received dataset in a secure enclave In accordance with other aspects of this particular embodiment, the method further comprises re-training the trained machine learning model using the dataset, wherein prior to re-training the trained machine learning model is locked with respect to a first demographic, and wherein after re-training the trained machine learning model is locked with respect to a heuristically generated different demographic associated with the dataset.

In accordance with other aspects of this particular embodiment, the method further comprises de-identifying the dataset in a stage of the secure pipeline.

In another particular embodiment, the techniques may be realized as a system for enabling a first party to provide a trained machine learning model to a second party comprising at least one computer processor communicatively coupled to and configured to operate in the system, wherein the at least one computer processor is further configured to perform the steps in the above-described method.

In another particular embodiment, the techniques may be realized as an article of manufacture for enabling a first party to provide a trained machine learning model to a second party comprising a non-transitory processor readable medium and instructions stored on the medium, wherein the instructions are configured to be readable from the medium by at least one computer processor and to thereby cause the at least one computer processor to operate so as to perform the steps in the above-described method.

The invention claimed is:

1. A method for enabling a first party to provide a trained machine learning model to a second party, the method comprising:
   receiving the trained machine learning model from the first party, the trained machine learning model being associated with one or more policies defining permissible operations;
   constraining the second party to operate the trained machine learning model in a manner that is consistent with said one or more policies;
   collecting, by a program operating in a secure enclave serving as a nth-stage of a secure pipeline, a dataset;
   transmitting said dataset to a (n−1) stage of said secure pipeline; and
   re-training the trained machine learning model using the dataset, wherein prior to re-training the trained machine learning model is locked with respect to a first demographic, and wherein after re-training the trained machine learning model is locked with respect to a heuristically generated different demographic associated with the dataset.

2. The method of claim 1, further comprising encapsulating the trained machine learning model within a secure enclave.

3. The method of claim 2, wherein the secure enclave is connected to a first stage of a secure data pipeline.

4. The method of claim 3, wherein the first stage accepts an output of another data pipeline.

5. The method of claim 4, wherein the first stage is connected to an input of a second stage data pipeline.

6. The method of claim 1, further comprising:
collecting operational data associated with the second party operating the trained machine learning model; and
storing the operational data under control of a secure enclave thereby restricting access to the operational data to one or more authenticated parties.

7. The method of claim 6, further comprising permitting additional data to be added to the operational data by the one or more authenticated parties.

8. The method of claim 7, further comprising attaching at least one digital certificate to the additional data.

9. The method of claim 1, wherein the (n−1) stage of said secure pipeline processes the received dataset in a secure enclave.

10. The method of claim 1, further comprising de-identifying the dataset in a stage of the secure pipeline.

11. A system configured to allow a first party to provide a trained machine learning model to a second party, the system comprising:
a non-transitory memory; and
one or more processors configured to read instructions from the non-transitory memory, the instructions causing the one or more processors to perform operations comprising:
receiving the trained machine learning model from the first party, the trained machine learning model being associated with one or more policies defining permissible operations;
constraining the second party to operate the trained machine learning model in a manner that is consistent with said one or more policies;
collecting, by a program operating in a secure enclave serving as a nth-stage of a secure pipeline, a dataset;
transmitting said dataset to a (n−1) stage of said secure pipeline; and
re-training the trained machine learning model using the dataset, wherein prior to re-training the trained machine learning model is locked with respect to a first demographic, and wherein after re-training the trained machine learning model is locked with respect to a heuristically generated different demographic associated with the dataset.

12. The system of claim 11, wherein the operations further comprise encapsulating the trained machine learning model within a secure enclave.

13. The system of claim 11, wherein the operations further comprise:
collecting operational data associated with the second party operating the trained machine learning model; and
storing the operational data under control of a secure enclave thereby restricting access to the operational data to one or more authenticated parties.

14. The system of claim 13, wherein the operations further comprise permitting additional data to be added to the operational data by the one or more authenticated.

15. The system of claim 11, wherein the operations further comprise de-identifying the dataset in a stage of the secure pipeline.

16. A non-transitory computer readable medium storing instructions that, when executed by one or more processors, cause the one or more processors to perform operations comprising:
receiving a trained machine learning model from a first party, the trained machine learning model being associated with one or more policies defining permissible operations;
constraining a second party to operate the trained machine learning model in a manner that is consistent with said one or more policies;
collecting, by a program operating in a secure enclave serving as a nth-stage of a secure pipeline, a dataset;
transmitting said dataset to a (n−1) stage of said secure pipeline; and
re-training the trained machine learning model using the dataset, wherein prior to re-training the trained machine learning model is locked with respect to a first demographic, and wherein after re-training the trained machine learning model is locked with respect to a heuristically generated different demographic associated with the dataset.

17. The non-transitory computer readable medium of claim 16, wherein the operations further comprise encapsulating the trained machine learning model within a secure enclave.

18. The non-transitory computer readable medium of claim 16, wherein the operations further comprise:
collecting operational data associated with the second party operating the trained machine learning model; and
storing the operational data under control of a secure enclave thereby restricting access to the operational data to one or more authenticated parties.

19. The non-transitory computer readable medium of claim 18, wherein the operations further comprise permitting additional data to be added to the operational data by the one or more authenticated parties.

20. The non-transitory computer readable medium of claim 17, wherein the operations further comprise de-identifying the dataset in a stage of the secure pipeline.

* * * * *